United States Patent [19]

Pastura et al.

[11] 4,280,012

[45] Jul. 21, 1981

[54] METHOD OF REMOVING CHLORINATED PHENOL IMPURITIES

[75] Inventors: Albino Pastura, Herdecke; Gerhard Kelbch, Witten; Hans-Leo Hülsmann, Wetter, all of Fed. Rep. of Germany

[73] Assignee: Dynamit Nobel Aktiengesellschaft, Troisdorf, Fed. Rep. of Germany

[21] Appl. No.: 16,477

[22] Filed: Mar. 1, 1979

[30] Foreign Application Priority Data

Mar. 9, 1978 [DE] Fed. Rep. of Germany ....... 2810142
Apr. 1, 1978 [DE] Fed. Rep. of Germany ....... 2814126

[51] Int. Cl.³ ..................... C07C 37/70; C07C 39/26
[52] U.S. Cl. ..................................... 568/755; 568/725
[58] Field of Search ............................ 568/755, 725

[56] References Cited

U.S. PATENT DOCUMENTS

| | | | |
|---|---|---|---|
| 2,829,175 | 4/1958 | Bowman et al. | 568/725 |
| 3,816,268 | 6/1974 | Watson et al. | 568/755 |
| 3,909,365 | 9/1975 | Christena | 568/755 |
| 4,016,047 | 4/1977 | Christena | 568/755 |

*Primary Examiner*—Werren B. Lone
*Attorney, Agent, or Firm*—Sprung, Felfe, Horn, Lynch & Kramer

[57] ABSTRACT

A method of removing an impurity of the group chlorinated dibenzo-p-dioxins, chlorinated dibenzofurans, chlorinated hydroxydiphenylethers and chlorinated diphenylethers from a substance containing the same which comprises contacting said substance with an agent which is hydrazine, acetylene, an acetylene derivative or a compound which under the processing conditions is a source of hydrazine or acetylene.

24 Claims, No Drawings

METHOD OF REMOVING CHLORINATED PHENOL IMPURITIES

BACKGROUND OF THE INVENTION

1. FIELD OF THE INVENTION

This invention relates to an easy and practical method for the removal of highly undesirable halogenated polycyclic compounds inevitably produced in the commercial production of halogenated phenols such as tetrachlorophenol and pentachlorophenol. More especially, this invention relates to the detoxification of residues obtained in the production of halogenated phenols by contacting substances containing the same with compounds containing carbon to carbon triple bonds.

2. DISCUSSION OF THE PRIOR ART

Of the more highly chlorinated phenols produced on a large technical scale by various methods, such as the chlorination of phenol or the hydrolysis of hexachlorobenzene, great importance has been acquired by tetrachlorophenol and pentachlorophenol and their derivatives. They are primarily fungistatic, but also have a bactericidal action, and they are used to a considerable extent in the building industry, in a variety of industrial processes and in agriculture, for example as wood protecting and preserving agents, as agents for the treatment of woods which can be attacked by microorganisms causing blue rot, as agents for combatting slime mold in the paper industry and other industries, and as harvesting aids, for example in the harvesting of cotton.

Under favorable conditions, impurities can be formed, some of which are toxic, from technical polychlorinated phenols. These impurities can be divided into four groups:

1. Chlorinated dibenzo-p-dioxins
2. Chlorinated dibenzofurans
3. Chlorinated hydroxydiphenylethers (predioxins and isopredioxins)
4. Chlorinated diphenylethers.

The toxicity of the first-named group of compounds is known; that of the other groups of compounds is considerably lower, but is not yet clearly understood.

The chlorinated dibenzo-p-dioxins, but also the substances of the third and fourth group are polychlorinated polycyclic aromatic or heteroaromatic substances which are extremely stable and very difficult to attack chemically. Attempts have been made to accelerate the decomposition of these substances by the action of ultraviolet light, in some cases with additional treatment with olive oil, but the effect and the rate of decomposition are poor.

A technically practicable method of rapidly destroying the above-named impurities has not been known hitherto.

SUMMARY OF THE INVENTION

In accordance with this invention, the aforementioned impurities are removed from substances containing the same by contacting said substances with a compound possessing a carbon to carbon triple bond or a compound which under the processing conditions supplies a compound possessing a carbon to carbon triple bond. Thus, in accordance with this invention, impurities of the groups cited above are removed from a substance containing the same by a process which comprises contacting said substance with an agent which is hydrazine, acetylene, and acetylene derivative or a compound which under the processing conditions is a source of hydrazine or acetylene. Mixtures of hydrazine, acetylene, acetylene derivatives, etc. can, of course, be employed.

It should be understood that the process of the invention removes the aforementioned impurities by converting such impurities to any of several different forms as will appear from the ensuing disclosure. Thus, these impurities are "removed" by virtue of the fact that they are converted into a form. These new forms possess substantially less toxicity than the unconverted impurities.

In carrying out the process, the "substance" which contains the impurity can be a chemical composition in which in addition to any one of the described impurities there are present other materials. The "substance" can also include the walls of a reactor, a reaction vessel, a pipe or other conduit which has become coated with any of the named impurities, a spray nozzle or any other surface to which any of the described impurities adhere. Thus, the word "substance" is to be construed broadly. The underlying concept is that the impurity is converted by the use of the hydrazine, acetylene or acetylene derivative to another form, generally a highly viscous or even resinous form.

Treatment agents which can be used in accordance with the invention include especially aqueous hydrazine solutions containing up to 80% hydrazine by weight, preferably the easily available aqueous solutions containing from 60 to 80 weight-percent of hydrazine, as well as the commercial solution containing approximately 80%.

Furthermore, solutions and in some cases emulsions for suspensions of hydrazine in other solvents of dispersants, such as alcohols such as methanol or ethanol can be used. Alkyl or aryl hydrazines in which one or both of the $NH_2$ groups of hydrazine are replaced by an alkyl moiety or an aryl moiety can also serve as treatment agents. If desired, hydrazonium salts can also be used, especially hydrazonium hydrochloride or its solutions.

The treatment agents are in general to have a content of hydrazine or hydrazine derivates which will permit an effective reaction with the impurities. Accordingly, in some cases dilutions down to 20 to 60% by weight can be effected.

Also suitable as treatment agents are substances which contain the ethynylene group —C≡C— or can form this group, and therefore also substances having a reactive carbon triple bond, especially acetylene or organic or salt-like acetylene derivatives. These include straight or branched chain aliphatic compounds which can be hydrocarbons or can contain oxygen, sulphur or nitrogen in the chain. These compound have between 2 and 18 C atoms and can also contain any one or more of the following functional groups:

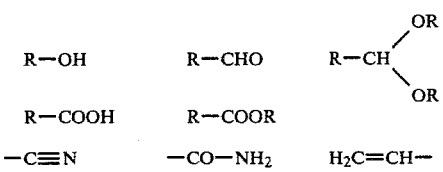

They can be substituted or unsubstituted. When substituted they can be substituted in any one of the following substituents particularly contemplated types of aliphatic compounds are those which fall within the following sub-generic classes:

alcoholes, esters, acids and acid amides.

Of these particularly contemplated compounds include the following:

alkin groups containing acids, fatty oils, diols and cyaneamides.

If during the process liberation of acetylene or other ethynylene derivative is necessary, the process can be performed with water or steam, in some cases with atmospheric moisture, or, for example, with acids.

Salt-like carbides, especially the alkaline and/or alkaline earth metal salts of acetylene can be used as inorganic acetylene derivatives which react in the presence of water to release acetylene. An economical salt that is available in large amounts is calcium carbide. It is therefore used preferentially. Other contemplated carbides include:

alcali metal carbides and alcali earth metal carbides

Examples of organic acetylene derivatives and substances containing the ethynylene group are acetylene dicarboxylic acid esters, e.g., alkyl ester, propiolic acid esters and oils of natural origin containing alkyne groups, such as for example boleko oil, camomile oil from Matricaria inodorata, or the etheral oil from Artemisia vulgaris.

Numerous other derivatives containing carbon triple bonds are also effective but are less preferable only because they are to some extent difficult to obtain. These include:

polyine and their derivates

The reaction takes place even at room temperature, but the temperature can be between 20° and 200° C. Elevated temperatures between 30° C., and in some cases the boiling point of the reaction mixture, are advantageous for a fast reaction.

The process is normally carried out at atmospheric pressure. However, it can be carried out up to pressures as high as 15 atmospheres. Generally speaking, the process is performed over a period of time between 15 and 480 minutes preferably between 60 and 360 minutes with temperature and pressure being variables effecting the time.

The action of light, in some cases of visible light, or especially of ultraviolet light, accelerates the reaction, and this is especially valuable when temperatures between 20° and about 40° C. are to be applied.

The residues to be treated by this process or the substances containing these residues are especially the distillation residues from the preparation of penta- and tetrachlorophenol. If desired, residues from the chlorination of other phenols and of the bromination of phenols can also be used for the purpose.

The pentachlorophenol that is marketed commercially does not require treatment, generally, since it is free of the above-named residues.

Furthermore, laboratory apparatus, kettles, parts of apparatus, etc., which have been used in experiments or tests can be treated by this process.

The substances to be treated can be, in the widest sense, any objects which have intentionally or accidentally come into contact with especially the substances of the first two groups of substances mentioned in the beginning. It is to be remembered that the impurities almost without exception are in a very low concentration in or on a material which of itself does not need treatment. It must furthermore be considered that even the very low concentration of the impurities can vary very widely; while the concentration in raw chlorination products of phenols is very low, higher concentrations do occur, for example, in residues from refinement processes.

The treatment can be preceded, if desired, by a concentration of the residues, for example by extraction, absorption with solvents such as benzene or methylene chloride, or distillation.

The treatment measures performed in accordance with the present process therefore must take into account various contents of other materials which may be inert with respect to the treatment agents or which might react with them.

In general, therefore, an excess of the treatment agent is always to be used. In the case of samples containing substances of an unknown chemical nature, a great excess of the treatment agent, amounting to as much as 2 to 5 weight-parts per weight-part of the materials to be treated, is desirable. In the case of materials which are known and materials containing large proportions of substances which are inert during the treatment, the amount of treatment agent can be reduced considerably, down to, say, 0.1 to 2.0 weight-parts or less per weight part of the materials being treated. An analysis of the material, by gas chromatography, for example, is desirable.

In general a single treatment will suffice, but two treatments may be desirable, especially for the removal of small residues. Three treatments are necessary only in exceptional cases.

The treatment agent and the substances being treated are to be mixed together thoroughly for the reaction. If the treatment agents are solids, such as the carbides, for example, they are to be ground or finely pulverized. The action of liquid treatment agents used, for example, by spraying or dipping, can be assisted by means of surface active substances.

The treatment can be preceded, if desired, by a concentration of the residues, for example by extraction, dissolution in solvents such as benzene or methylene chloride, or distillation.

Hot water or steam can be added during the treatment.

The treatment can be assisted, if desired, by the additional action of metal catalysts in amounts generally of 0.001 to 0.05, preferably 0.005 to 0.02, percent of metal with respect to the weight of the hydrazine.

The catalysts can be used in the form of metals or metal compounds such as oxides or salts, either unsupported or on supports such as ceramic oxides, $SiO_2$, $BaSO_4$ or the like.

Metals of Group VIII of the Periodic Table of the Elements, such as iron, cobalt, nickel, ruthenium, rhodium, palladium and platinum can be used, although other catalyst metals which enhance the reactivity of hydrazine, such as vanadium, can be used. Vanadium and palladium supported, for example, on barium sulfate, have been found to be very effective.

The action of the treatment agents is high even at room temperature, but it can be improved by temperatures in the range from 20° to 50° C., or in some cases up to 90° C.

When carbides are used, water in liquid form, as steam, or in some cases in the form of atmospheric humidity, is necessary in order to liberate acetylene. An excess of water is often desirable.

The action of acetylene itself or of compounds containing ethynylene groups can be enhanced by water, although water is not a requirement.

The treatment can be conducted such that, using excesses of the treatment agent and, in some cases, of water, the treatment is completed in a few minutes. It is desirable to perform such a treatment in a closed vessel, such as for example a reactor, which is preferably equipped with a stirrer and, if desired, with a means for removing excess acetylene.

The treatment can also be performed merely by sprinkling solid treatment agents or by the application of liquid treatment agents, by spraying for example, in situ in some cases. In this treatment it is possible to use less than the necessary amount of the treatment agent and to repeat the treatment one or more times. Water or steam can be used additionally, although the liberation of the acetylene can also be left to the action of atmospheric humidity. Long treatment times of several hours or days are possible, without undesirable effects.

The simultaneous action of light in the visible range or of ultraviolet light is often desirable and can substantially accelerate the reaction. In the case of treatment in closed vessels, and in some cases treatments in situ, the additional action of ultraviolet light is desirable; in the case of in situ treatments, daylight or the light from any kind of light source is desirable.

Single treatments can remove 90 to 98% of the impurities originally present, and a virtually complete removal can be achieved by two treatments.

The success of the treatment can be determined by extracting the neutral contents with solvents after transforming the phenolic contents to the salts, and analyzing the extracts of the treated specimens in comparison with extracts of the untreated specimens.

In samples treated with acetylene or acetylene derivatives, highly viscous substances were extracted in one series, which had several times the molecular weight of the impurities. In these highly condensed substances which had evidently formed by the reaction of acetylene or acetylene derivatives with the impurities, the residues are no longer detectable or are detectable in only very small amounts in comparison to the original amounts. Only small amounts of highly viscous substances can be extracted from other treated specimens, especially after two treatments, and these substances no longer contain any of the original residues; evidently most of the substances formed in the treatment are so greatly condensed that extraction with solvents is no longer possible.

In the treatment performed with hydrazine, brown, viscous masses form which contain nitrogen. These masses can amount to several times the amount of the original impurities, which is to be attributed in part to the reaction of hydrazine with substances which accompany the impurities. The residue contains two groups of products of the reaction with hydrazine: the one, viscous part evidently consists of relatively high molecular weight condensation products of the impurities, while the other part, of the low molecular weight, evidently is formed by reactions of the hydrazine in which the molecules of the impurities are cleaved.

In order to more fully illustrate the nature of the invention in a manner of practicing the same, the following examples are presented:

EXAMPLES

EXAMPLE 1

(a) 100 grams of a technical pentachlorophenol prepared at elevated temperature is completely dissolved in 60 ml of benzene. This solution extracted in a two-liter separatory funnel with 600 ml of a 5 wt-% solution of soda lye. The benzene phase is separated and dried with anhydrous sodium sulfate. After removal of residual amounts of chlorophenols by column chromatography, the solution is concentrated by evaporation on the water bath. The small evaporation residue obtained is soluble in numerous organic solvents which are typical for the dissolution of organic neutral substances of low molecular weight, for example in aromatic and aliphatic hydrocarbons such as benzene, and in chlorinated hydrocarbons such as methylene chloride or ethers such as diethyl ether. The evaporation residue contains the impurities mentioned in the beginning. The aqueous phase contains the chlorinated phenols and gas chromatography shows it to be free of the named impurities.

(b) A 0.2 gram sample collected from these evaporation residues is dissolved in 10 ml of methylene chloride and placed in a flask equipped with a stirrer. 0.5 g of calcium carbide in finely pulverized form is added with constant stirring at room temperature in three portions over a period of two minutes. After each addition of calcium carbide, 50 ml of water is added. After the mixture has been allowed to react for 5 minutes at room temperature, it is exhaustively extracted with methylene chloride and the extract is subjected to gas chromatography.

In comparison with the gas chromatogram of an untreated sample of the evaporation residue, only by increasing the sensitivity of the detector can any of the original components be recognized in the extract of the treated sample.

From a comparison of the intensities, it is concluded that at least 95% of the impurities are no longer contained in the extract of the treated sample.

EXAMPLE 2

A 0.2 g sample of the evaporation residue obtained in accordance with Example 1b is treated as in that Example, but is heated at 35° C. during the treatment. On the basis of the gas chromatogram it is concluded that 95 to 97% of the impurities have been destroyed by the treatment.

EXAMPLE 3

A 0.2 g sample of the evaporation residue of Example 1a is treated with calcium carbide as in Example 1b, but steam was introduced into the flask for a period of 10 minutes until the weight had been increased by 2.5 grams.

The gas chromatogram after the treatment is the same as that of Example 1b.

EXAMPLE 4

Fifty-gram samples of material containing chlorinated phenol impurities were tested. An extraction test showed that about 2% of extractable substance was present, plus 98% of substances which were inert in the extraction.

The gas chromatogram showed chlorinated phenols in addition to very small amounts corresponding to the impurities of the evaporation residue of Example 1a.

A portion of the sample was treated as in Example 1b. After the treatment no more impurities could be found in the gas chromatogram.

A portion of the sample was extracted as in Example 1a and the evaporation residue was treated as in Example 2. The impurities were no longer to be found in the gas chromatogram.

Samples of the same material were spread onto areas of 0.2 m² each and (a) sprinkled uniformly with 30 g of finely powdered calcium carbide or (b) uniformly sprayed with 50 g of acetylene dicarboxylic acid dimethyl ester. Then the surfaces were sprayed with 100 ml of water each. After two days 50 gram samples were taken and tested as above. There were no indications of any remaining impurities.

EXAMPLE 5

The porous sieve serving for the distribution of chlorine was removed from a reactor used for the chlorination of phenols. The sieve was dipped into a tank containing three liters of methanol having a water content of 5% by weight, and calcium carbide was added, with stirring, in four portions of 20 g each over a period of 20 minutes. During the treatment the surface of the tank was exposed to ultraviolet light.

After the treatment, the sieve was boiled in benzene and the benzene was concentrated by evaporation. A very small amount of evaporation residue was dissolved in 2 ml of benzene.

The residue from the treatment was exhaustively extracted with methylene chloride. The concentration residue of the extract was dissolved in 2 ml of benzene.

None of the named impurities was found in the gas chromatogram of either of the benzene solutions.

EXAMPLE 6

A 0.3 g sample of the evaporation residue of Example 1a was treated for 10 minutes with 0.5 g of calcium carbide in three portions with the addition of 10 ml of water, under ultraviolet light. After the treatment the residue was completely extracted with diethyl ether and concentrated by evaporation. The residue amounted to 0.16 g and consisted mainly of poorly soluble, highly viscous substances which had evidently been formed by the reaction of the acetylene with the impurities. The gas chromatogram of the highly viscous concentration residue contained the bands typical of the original evaporation residue at a very low intensity. It was concluded that at least 95% of the impurities of the original concentration residue had reacted. The treatment was repeated in the presence of ultraviolet light with the residue of the first treatment and with the extract of the first treatment. After extraction and concentration as above, only 0.008 g and 0.006 g, respectively, of the concentration residue were found. No impurities at all were found in the gas chromatogram. In the extraction of the again-treated extract from the first treatment, a large portion of very highly condensed substances was found, which could no longer be extracted; even the extractable portion consisted almost exclusively of highly condensed substances.

EXAMPLE 7

0.5 g of oleic acid-2,4,7,9-tetramethyl-5-decin-4,7-diol-diester was dissolved in methylene chloride with 0.2 g of extract from pentachlorophenol. The solution was irradiated with ultraviolet light for two hours. Due to the irradiation, a highly viscous mass was formed, which consisted of addition products of acetylene ester with the by-products of pentachlorophenol. The impurities were no longer detectable in the gas chromatogram.

EXAMPLE 8

(a) 100 g of a technical pentachlorophenol produced at high temperature is completely dissolved in 600 ml of benzene. This solution is extracted in a two-liter separatory funnel with 600 ml of 5 wt.-% aqueous soda lye. The benzene phase is separated and dried with anhydrous sodium sulfate. After the removal of residual amounts of chlorophenols by column chromatography, the solution is concentrated by evaporation on the water bath. The small evaporation residue is soluble in numerous organic solvents typically used for the dissolution of low molecular weight organic neutral substances, for example in aromatic and aliphatic hydrocarbons such as benzene, chlorinated hydrocarbons such as methylene chloride, or ethers such as diethyl ether. The evaporation residue contains the neutral portions including the impurities mentioned above. The aqueous phase contains the chlorinated phenols and according to gas chromatography tests it is free of the above-mentioned impurities.

(b) A sample of 0.3 g of the evaporation residues collected in accordance with (a) above is transferred to a flask provided with a stirrer, after it has been dissolved in 10 ml of methylene chloride as the rinsing and transfer agent. 20 g of hydrazine hydrate (80% solution by weight) is added with stirring and the mixture is irradiated with ultraviolet light. The temperature of the solution rises to 40° C. After evaporation, a very viscous, brown, nitrogen-containing residue is obtained, whose weight, due to reaction with hydrazine, amounted to several times that of the original sample. The residue is exhaustively extracted with methylene chloride at room temperature.

According to the gas chromatogram and infrared spectrum, the residue consists of products of the addition of hydrazine onto the impurities and having a high molecular weight, and of cleavage products of low molecular weight containing nitrogen, formed by the action of hydrazine. The original impurities are no longer detectable.

EXAMPLE 9

0.3 of extraction residue of Example 8b was treated with 5 ml (80 wt.-% solution) of hydrazine hydrate. After irradiation, a dry, viscous residue remained, which was again extracted with methylene chloride and analyzed.

1st weighing of extract: 0.2483 g. Then approximately 0.2 g of the first weigh-out of the extract was again treated, extracted and analyzed.

2nd weighing of extract: 0.1168 g.

All of the extraction residues are highly cleaved products as well as reaction products formed by the substances with hydrazine. The residues are all viscous and brown, and they contain nitrogen.

The infrared spectrum shows that a complete change in the chemical structure of the neutral substances has taken place.

EXAMPLE 10

Example 8b is repeated, and 0.3 g of residue is treated as follows:

(a) at 40° C. with 15 ml of 70 wt-% hydrazine solution
(b) at 40° C. with 20 ml of 65 wt-% hydrazine solution
(c) at 90° C. with 30 ml of 60 wt-% hydrazine solution, dissolved in a mixture of ethanol and water (40:60 parts by weight).

The analyses of the treatment residues gave the same results as described in Example 8b.

EXAMPLE 11

Example 8b is repeated, but the treatment is performed at 120° C. in the absence of ultraviolet light. The peaks of the original neutral components are no longer visible in the gas chromatogram of the residue.

EXAMPLE 12

50 g of technical pentachlorophenol was dissolved on the water bath in 200 ml of hydrazine hydrate (approximately 80 wt-% solution) and refluxed for 1.5 hours. The solution was then exhaustively extracted with methylene chloride.

| Extraction residue: | 1.9670 g = 3.9% of the original sample. |
|---|---|

The extract consists of a very viscous mass containing nitrogen. Analyses show that this mass is a mixture of cleavage and reaction products of the accompanying substances with hydrazine.

The impurities present in small amounts in the methylene extract of the original sample were no longer detectable after the treatment.

EXAMPLE 13

The solution of pentachlorophenol in hydrazine was boiled on the water bath, using the following catalysts:
(a) 0.02 g Pd/BaSO$_4$ (10 wt.-% solution)
(b) 0.002 g Palladium powder
(c) 0.01 g of V/Al$_2$O$_3$ (5 wt.-% solution).

The reaction time was shortened to one-half, while the results were the same as in Example 12.

What is claimed is:

1. A method of removing an impurity of the group chlorinated dibenzo-p-dioxins, chlorinated dibenzofurans, chlorinated hydroxydiphenylethers and chlorinated diphenylethers from a halogenated phenol composition containing said impurity which comprises contacting at 20° to 200° C. under a pressure of normal up to 15 atmospheres said composition containing halogenated phenol with 0.5 to 5 weight percent of an agent which is hydrazine, acetylene, or a compound which under the processing conditions is a source of hydrazine or acetylene.

2. A method according to claim 1 wherein said agent is an acetylene derivative and said derivative is a compound having the ethynylene group —C≡C—.

3. A method according to claim 1 wherein said agent is a carbide which under the processing conditions releases acetylene.

4. A method according to claim 3 wherein said carbide is an alkaline or alkaline earth metal salt of acetylene.

5. A method according to claim 4 wherein said carbide is calcium carbide.

6. A method according to claim 1 wherein said agent is an organic acetylene derivative and said derivative is an acetylene dicarboxylic acid ester.

7. A method according to claim 1 wherein said agent is an organic acetylene derivative and said derivative is propiolic acid ester.

8. A method according to claim 1 wherein said agent comprises a naturally occurring oil containing an alkyne group.

9. A method according to claim 8 wherein said oil comprises a boleko oil, camomile oil from Matricaria inodorata or the ethereal oil from Artemisia vulgaris.

10. A method according to claim 1 wherein said agent is hydrazine.

11. A method according to claim 1 wherein the method is carried out in the presence of water.

12. A method according to claim 1 wherein after said substance is contacted with said agent water is added.

13. A method according to claim 11 wherein the method is carried out with application of heat.

14. A method according to claim 1 wherein ultraviolet light is applied to said substance during or after treatment of said substance with said agent.

15. A method according to claim 1 wherein the method is carried out in the presence of a catalyst comprising a metal or its compound.

16. A method according to claim 15 wherein said catalyst is a metal of Group VIII of the Periodic Table of the Elements or a compound thereof.

17. A method according to claim 15 wherein said catalyst comprises vanadium or a compound thereof.

18. A method according to claim 1 wherein the agent is acetylene.

19. A method according to claim 1 wherein said agent comprises a salt of acetylene and said method is carried out in the presence of water.

20. A method according to claim 1 wherein said substance is treated with an organic alkyne.

21. A method according to claim 20 wherein said organic alkyne is dissolved in an inert solvent.

22. A method according to claim 3 wherein said carbide is in a finely divided form and the method takes place in the presence of liquid or vaporous water.

23. A method according to claim 1 wherein said halogenated phenol is pentachlorophenol.

24. A method according to claim 1 wherein said halogenated phenol is tetrachlorophenol.

* * * * *